United States Patent
Christophe

(10) Patent No.: US 11,152,122 B2
(45) Date of Patent: Oct. 19, 2021

(54) SYSTEM AND METHOD FOR EVALUATING VASCULAR RISKS

(71) Applicant: CASIS—CARDIAC SIMULATION & IMAGING SOFTWARE, Dijon (FR)

(72) Inventor: Jean-Joseph Christophe, Dijon (FR)

(73) Assignee: CASIS—CARDIAC SIMULATION & IMAGING SOFTWARE, Dijon (FR)

( * ) Notice: Subject to any disclaimer, the term of this patent is extended or adjusted under 35 U.S.C. 154(b) by 335 days.

(21) Appl. No.: 16/477,846

(22) PCT Filed: Jan. 25, 2018

(86) PCT No.: PCT/EP2018/051851
§ 371 (c)(1),
(2) Date: Jul. 12, 2019

(87) PCT Pub. No.: WO2018/141628
PCT Pub. Date: Aug. 9, 2018

(65) Prior Publication Data
US 2019/0371473 A1    Dec. 5, 2019

(30) Foreign Application Priority Data
Feb. 2, 2017  (FR) ...................................... 1750859

(51) Int. Cl.
*G16H 50/30*     (2018.01)
*G16H 30/20*     (2018.01)
*G16H 50/20*     (2018.01)
*A61B 5/00*      (2006.01)

(52) U.S. Cl.
CPC ............... *G16H 50/30* (2018.01); *A61B 5/00* (2013.01); *G16H 30/20* (2018.01); *G16H 50/20* (2018.01)

(58) Field of Classification Search
CPC ..................................................... G16H 50/30
See application file for complete search history.

(56) References Cited

U.S. PATENT DOCUMENTS

| | | | |
|---|---|---|---|
| 8,812,431 | B2 | 8/2014 | Voigt et al. |
| 9,345,442 | B2 | 5/2016 | Ohishi |
| 9,349,178 | B1 | 5/2016 | Itu et al. |
| 2009/0088624 | A1 | 4/2009 | Nussbaumer |
| 2015/0164342 | A1* | 6/2015 | Choi ................. A61B 5/02007 600/407 |

OTHER PUBLICATIONS

Kolachalama, et al., "Mining data from hemodynamic simulations via Bayesian emulation", BioMedical Engineering OnLine, vol. 6, No. 47, 2007.

(Continued)

*Primary Examiner* — Evangeline Barr
*Assistant Examiner* — Jordan L Jackson
(74) *Attorney, Agent, or Firm* — BakerHostetler

(57) ABSTRACT

A method (and the associated system) for risk evaluation in a vascular region of interest V are provided, making it possible, based on a fluidic study and/or on a treatment algorithm using a learning method, to generate risk models MR predictively indicating the risk level NR for the occurrence of events such as: occurrence and rupture of an aneurysm, coarctation, etc., and the associated anatomical areas. The models MR are intended to serve as an assistance support for the medical decision-making of a physician.

18 Claims, 2 Drawing Sheets

(56) References Cited

OTHER PUBLICATIONS

Jankovic, et al., "Mining data from CFD simulations of aneurysm and carotid bifurcation models", J. of the Serbian Society for Computational Mechanics, vol. 6, No. 2, pp. 133-144, 2012.
Morizawa, et al., "Implementation of visual data mining for unsteady blood flow field in aortic aneurysm", J. Vis., vol. 14, pp. 393-398, 2011.
"Types of Mesh", Wikipedia, Jan. 25, 2017.
"Variance-based sensitivity analysis", Wikipedia, Nov. 13, 2016.
"Artificial neural network", Wikipedia, Jun. 11, 2016.
"Fluid-structure interaction", Wikipedia, Dec. 11, 2016.
"Machine learning", Wikipedia, Apr. 7, 2016.

\* cited by examiner

SYSTEM AND METHOD FOR EVALUATING VASCULAR RISKS

CROSS-REFERENCE TO RELATED APPLICATIONS

This application is a National Stage of International patent application PCT/EP2018/051851, filed on Jan. 25, 2018, which claims priority to foreign French patent application No. FR 1750859, filed on Feb. 2, 2017, the disclosures of which are incorporated by reference in their entirety.

FIELD OF THE INVENTION

The present invention pertains to the field of medical imaging and protocols for the analysis of afferent images. It relates more particularly to a method for evaluating and predicting aneurysm risks resulting in the formulation of risk maps that are intended to serve for example as an assistance support in the medical decision-making of a physician.

BACKGROUND

In the field of methods intended to evaluate and/or predict the occurrence or the evolution of a medical situation, methods and systems are known, such as the one presented for example in document U.S. Pat. No. 8,812,431 B2, that make it possible to compare an original medical model with a database of known cases, so as to find the closest cases and provide a basis for decision assistance for a physician.

In the specific context of the study of aneurysms, methods in which the prediction of the evolution of said aneurysm is based on the analysis of geometric data are also known, such as for example in documents US 2009088624 A and U.S. Pat. No. 9,345,442 B2.

Document US 2015/164342 discloses a method for evaluating vascular risk in which a learning algorithm is used to predict a vascular risk from a set of parameters whose numerical values are calculated from a fluid or mechanical model.

Document U.S. Pat. No. 9,349,178 discloses a method for determining hemodynamic quantities by way of a trained learning method based only on synthetic data.

However, existing methods and systems more often than not use systems that are complex and/or expensive in terms of time and in terms of amounts of computing resources to be allocated, this exhibiting a major drawback, notably for medical structures of modest size.

Improving the prediction of the evolution of a pathology is a significant clinical concern for health professionals, in particular in the context of diagnosing and treating aneurysms, such as aortic aneurysms, and associated abnormalities such as aortic stenosis, coarctation of the aorta, or else deformations linked to a bicuspid aortic valve.

Specifically, there is excessive uncertainty with regard to the choice of the most appropriate treatment for each patient.

An aneurysm is usually defined as a permanent local swelling of an artery, with loss of parallelism of the boundaries.

At present, the most widespread methods for predicting a risk of rupture of an aneurysm essentially take into account geometric data specific just to the patient to be treated, such as the diameter of the aorta and the level of inflation of the aneurysm. These imprecise methods have well-known limits. Inter alia, they do not allow the physician to establish an accurate diagnosis, since firstly an aneurysm may rupture independently of the diameter of the impacted vascular region, an increase in the diameter of an artery does not automatically lead to a risk of aneurysm rupture, and by contrast, an aneurysm rupture may be triggered without having observed an increase in the diameter of the artery beforehand.

Due to this, it may be the case that said patient is for example operated on needlessly, or by contrast not operated on urgently when the risk of aortic rupture is at a critical level. Moreover, there is a permanent risk of rupture of an aneurysm, even in the absence of obvious symptoms, this being the case regardless of the dimensions of the aneurysm.

Other methods implementing studies of the blood flow of the patient have emerged, but these have two main drawbacks: the use of significant computing resources and a long data processing time.

SUMMARY OF THE INVENTION

The present invention intends to rectify the abovementioned drawbacks (poor accuracy, complexity, cost in terms of time and in terms of resources to be allocated) and provide decision assistance elements for physicians, by proposing a fast method that is able to be implemented in a very large number of medical imaging systems.

The evaluation method that is proposed relates to risk evaluation in a vascular region of interest V, such as the thoracic aorta, or the abdominal aorta.

It comprises two major solutions. The first (solution 1 or knowledge acquisition solution) concerns, broadly speaking (without limitation):

- developing and training a treatment algorithm using a learning method intended to generate risk models MR ($MR_A$, $MR_E$) as a decision assistance support for physicians, and
- preferably, evaluating the predictive capability of predictive (or non-predictive) parameters of a set of parameters JP to be analyzed, making it possible for example, and without limitation, to:
  - test the benefit and/or decide whether or not to include a new parameter in the set of parameters JP to be analyzed,
  - re-evaluate the predictive capability of the parameters of the set of parameters JP to be analyzed: some initial parameters may for example lose their predictive benefit when other new parameters deemed to be more effective are included in the set; it is then possible either to keep all of the parameters in the set or to exclude the parameters that have lost their predictive benefit,
- whereas the second solution (solution 2 or clinical application solution), broadly speaking, involves applying said treatment algorithm using a learning method to a patient so as to directly obtain, that is to say without excessively long calculations and/or with a small number of processing steps, at least one risk model MR as a decision assistance support for physicians.

The learning method may be for example a data mining method.

The transition between the knowledge acquisition (solution 1) and the clinical application (solution 2) preferably takes place when the set of parameters JP to be analyzed is fully formed, that is to say when all of the parameters are validated (their predictive capability being confirmed). Advantageously, the parameter(s) of the set of parameters JP to be analyzed is validated either:
- when it is input manually by the physician (and/or a user) and known to be validated, and/or via at least one evaluation and/or validation step L (described hereinafter).

Advantageously, regardless of the chosen solution, the set of parameters JP to be analyzed is independent of the patient.

According to variants, the step of generating risk model(s) MR (regardless of the step of the method in which it occurs) comprises:
- generating a model for at least one parameter of the set of parameters JP to be analyzed, and preferably for each of the parameters of the set of parameters JP to be analyzed, and/or
- generating a global model taking into consideration the simultaneous effect of a plurality of parameters of the set of parameters JP to be analyzed, and preferably all of the parameters of the set of parameters JP to be analyzed.

Advantageously, according to the invention, the step of generating a risk model MR associated with a parameter of the set of parameters JP to be analyzed comprises, inter alia, a step of assigning a risk level NR ($NR_A$, $NR_E$), from among a scale of risk levels, to each numerical item of data DN ($DN_A$, $DN_E$) calculated for said parameter of the set of parameters JP to be analyzed.

A risk level NR (from among a scale of risk levels) is preferably assigned to a set of numerical data DN ($DN_A$, $DN_E$) that are close in terms of:
- numerical values, and/or
- spatial distribution (numerical data calculated at contiguous points, for example at adjacent points in a mesh), and/or
- temporal distribution.

Advantageously, generating a global model comprises a step of determining and assigning a global risk level (from among a scale of risk levels), for example on the basis of a calculation involving, inter alia:
- the risk level NR associated with each parameter of the set of parameters JP to be analyzed,
- a weighting reflecting the relative influence of each parameter of the set of parameters JP to be analyzed.

The numerical data DN ($DN_A$, $DN_E$) are preferably calculated at each point of the corresponding mesh (that is to say: at each point of the mesh used in the calculation, if this mesh exists).

Advantageously, a risk level NR is assigned to each numerical item of data DN ($DN_A$, $DN_E$) at each point of the corresponding mesh (that is to say: at each point of the mesh used in the calculation, if this mesh exists).

Advantageously, the risk model MR is presented in a format containing visual markers allowing fast identification of risk areas (risk of occurrence of an aneurysm, risk of rupture of an aneurysm, risk of occurrence of a coarctation).

For example, the model may be in the form of a table of data, an image, a video, or a graph (curves, histograms, etc.) in which the numerical data are highlighted differently depending on the risk level NR to which they correspond.

For example, each risk level NR is associated with a particular visual marker, such as a color, a marking element, or any possible combination of visual markers.

The model preferably takes the form of a 3D map on which the visual markers are distributed and fused by risk level NR, for example when the visual markers are colored points, their "fusion" will give rise to flattened areas of the same color, making it very easy to quickly identify risk areas.

The model may also take the form of a 4D map (for example a 3D map fluctuating over time), allowing the risk evolution to be viewed over a given period.

Moreover, a person skilled in the art will know how to choose the rendering best suited to the model, depending on the targeted application.

DETAILED DESCRIPTION

Figure 1:
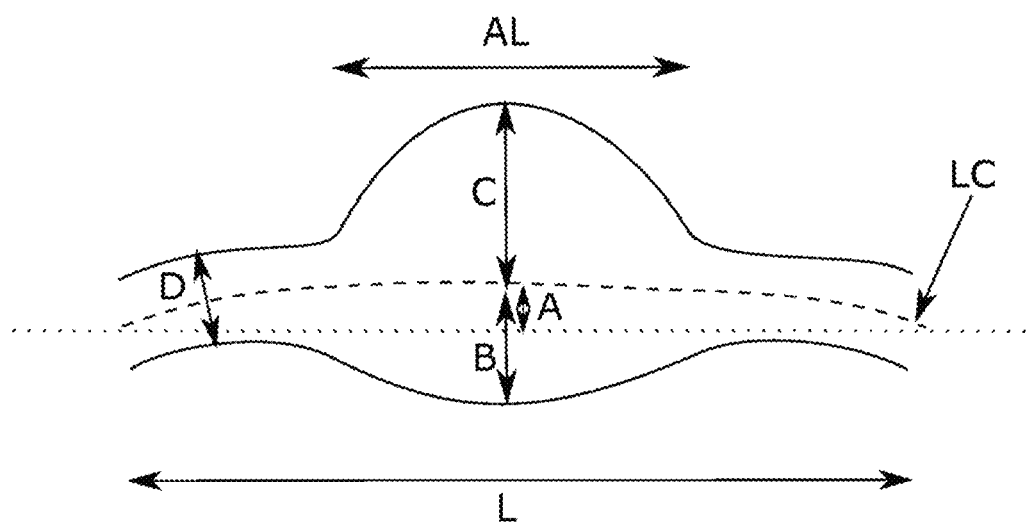
FIG. 1 is a diagram illustrating a vascular region of interest V, such as an aneurysm present in the aorta, and certain data in relation to its geometry.

Advantageously, as shown in FIG. 1, a fusiform aneurysm is described with reference to its center line LC, also called median line (in a reference frame based on the center line), which corresponds to a virtual line passing through the center of the aortic light.

It is also possible to describe it using data in relation to its geometry, such as:
- the exploration length L, that is to say the length corresponding to the total horizontal projection of said model M,
- the height A of the center line arc,
- the diameter D of the aorta,
- the inner radius B of the aneurysm (perpendicular to the center line LC of the aneurysm), which corresponds to the radius of the center line of the aorta to the inner wall of the aneurysm (that is to say the wall exhibiting the smallest bulge),
- the outer radius C of the aneurysm (perpendicular to the center line LC of the aneurysm), which corresponds to the radius of the center line of the aorta to the outer wall of the aneurysm (that is to say the wall exhibiting the greatest bulge),
- the length of the aneurysm AL, that is to say the average length of the aneurysm,
- a section of the aorta $S_c$ (not shown in FIG. 1).

The present invention may nevertheless also apply to aneurysms having other forms, such as saccular or polylobed aneurysms.

Figure 2:
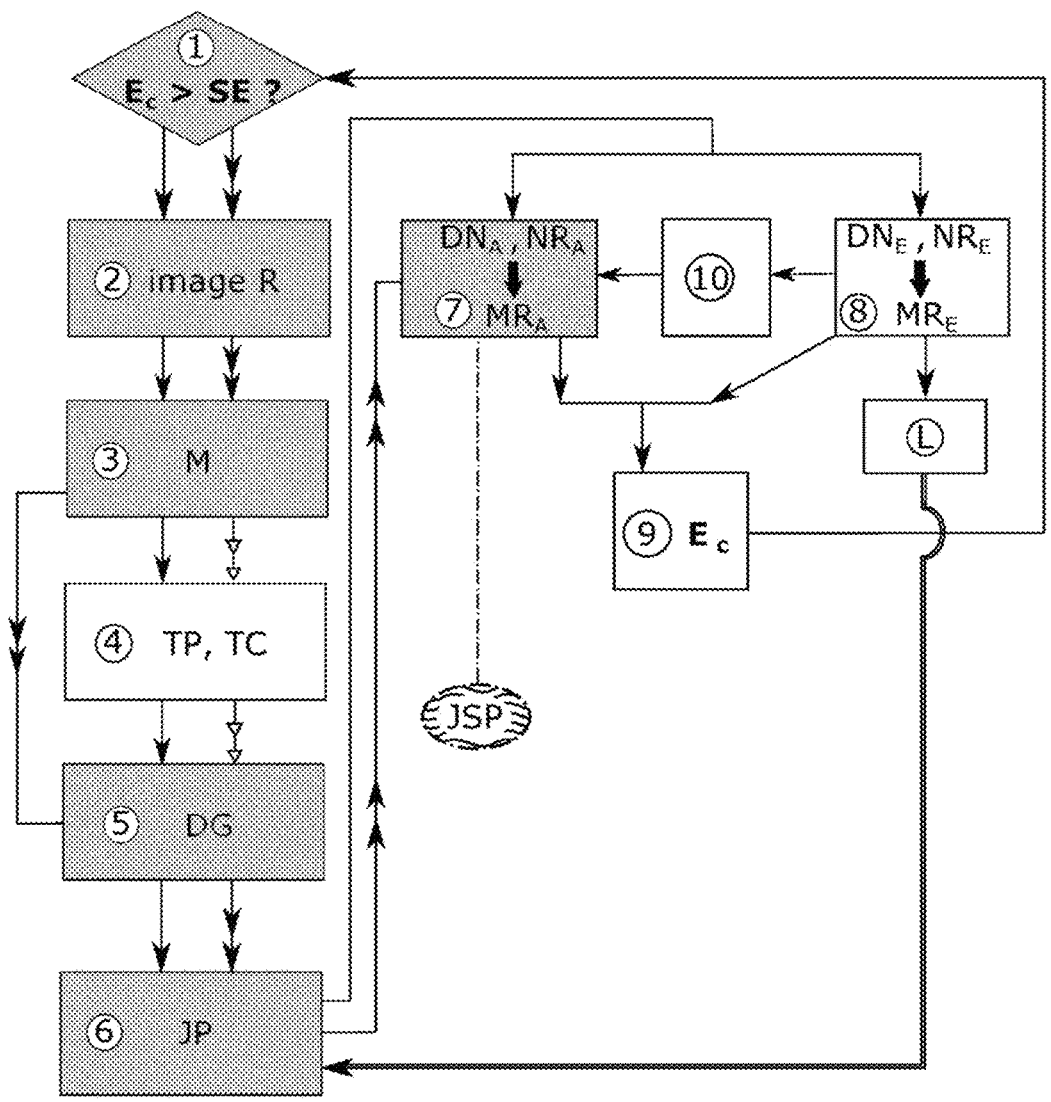
FIG. 2 is a diagram illustrating the main steps of the method according to the invention.

FIG. 2 is a diagram illustrating the steps of the method according to the invention.

Solution 1 of the method, which concerns at least the development and the acquisition of knowledge by the treatment algorithm using a learning method, is indicated by single black-headed arrows between the various steps (boxes) of the method that are involved.

Solution 2 of the method, which concerns the clinical application of said treatment algorithm using a learning method (and which involves applying said treatment algorithm using a learning method to a patient so as to directly obtain at least one risk model $MR_A$) is indicated by double black-headed and/or white-headed arrows between the steps (boxes) of the method that are involved, these being shaded.

Said method for risk evaluation in a vascular region of interest V, implementing a treatment algorithm using a learning method, is noteworthy in that it comprises the following steps for each successive patient case $P_i$ from among a group of patients $\{P_1, \ldots, P_i, \ldots, P_n\}$:

Step 1. testing the value of the predictive capability error $E_C$ of said treatment algorithm using a most recently known learning method (for example: recorded in memory or input by the physician), said value of the predictive capability error $E_C$ being defined so as to be greater than a predefined threshold SE in the first iteration of the method, and if the value of the error is greater than said predefined threshold SE: performing at least following steps 2 to 11 in this order, otherwise performing at least steps 2, 3, 5, 6 and 7 in this order. Preferably, when the value of the error $E_C$ is lower than said predefined threshold SE, performing at least steps 2, 3, 4, 5, 6 and 7 in this order.

Step 2. acquiring at least one representation R of a vascular region of interest V of said patient $P_i$, Step 3. reconstructing, from said representation R, at least one model M of said region of interest V from among: primary model MP, corrected model MC, Step 4. generating, from said model M, at least one mesh T (TP, TC) of said region of interest V, Step 5. extracting, from at least one model M resulting from step 3 and/or from at least one mesh T resulting from step 4, data DG in relation to the geometry of said vascular region of interest V, Step 6. Forming a set of parameters JP to be analyzed, so as to evaluate the risks in said region of interest V, from at least one pre-recorded list of predictive and/or non-predictive parameters, Step 7. determining the predictive risk numerical data $DN_A$, associated with at least one parameter of said set of parameters JP formed in step 6, by way of said treatment algorithm using a learning method, from at least the data DG in relation to the geometry of said vascular region of interest V, assigning a risk level $NR_A$ to said parameter (of said set of parameters JP), from among a scale of risk levels, and generating a risk model $MR_A$ in said region of interest V at least for each parameter of said set of parameters JP from said determined numerical data $DN_A$, Step 8. determining the predictive risk numerical data $DN_E$ ($DN_{EC}$, $DN_{EF}$), associated with at least one parameter of said set of parameters JP formed in step 6, through a fluidic study comprising at least one CFD (CFD: computational fluid dynamics) study, from at least one group of meshes comprising at least one mesh generated in step 4 and from at least one set of adapted input-output conditions SC, assigning a risk level $NR_E$ to said parameter (of said set of parameters JP) from among a scale of risk levels, and generating a risk model $MR_E$ ($MR_{EC}$, $MR_{EF}$) in said region of interest V at least for each parameter of said set of parameters JP from said determined numerical data $DN_E$ ($DN_{EC}$, $DN_{EF}$), Step 9. evaluating the predictive capability error $E_C$ of the treatment algorithm using a learning method in relation to the fluidic study, by comparing at least the results of steps 7 and 8, and recording the value of the capability error $E_C$, Step 10. training said treatment algorithm using a learning method by providing it at least with the results of step 8, Step 11. recording all of the data that are obtained in a patient case database in a data storage unit.

Advantageously, the generation of one (or more) risk model(s) $MR_A$ and/or $MR_E$ ($MR_{EC}$, $MR_{EF}$) in said region of interest V takes place when the method according to the invention adopts solution 1 and/or 2.

Preferably, the generation of one (or more) risk model(s) $MR_A$ and/or $MR_E$ ($MR_{EC}$, $MR_{EF}$) in said region of interest V takes place only when the method according to the invention adopts solution 2.

The method according to the invention is a method applied to a sample of patients $\{P_1, \ldots, P_i, \ldots, P_n\}$, that is to say that the method is applied to a first patient, and then to a second patient, and so on.

The steps that form said method are dynamic, depending on the value of the predictive capability error $E_C$ assigned to the treatment algorithm using a learning method that it uses.

The evaluation method thus first of all concerns developing and training a treatment algorithm using a learning method. This first solution of said method is adopted when the value of the predictive capability error $E_C$ assigned to the treatment algorithm by a learning method is greater than a predefined threshold SE, and involves performing at least steps 2 to 11 of said method, preferably in this order. As a variant, step 8, or steps 8 and 10, may be performed before step 7.

By way of indication, reaching this phase of the method requires acquiring and processing data from at least one hundred patients.

Then, when the value of the predictive capability error $E_C$ assigned to the treatment algorithm using a learning method drops below said predefined threshold SE, the evaluation method adopts a second solution that involves utilizing said treatment algorithm using a learning method. In this case, the evaluation method is formed at least of steps 2, 3, 5, 6 and 7, typically in this order.

In advanced variants of the method, additional steps may be inserted between the steps that are provided, but the initial steps will continue to be performed in the intended numerical order, subject to a possible reversal of the order of steps 7 and 8 and possibly 10, or even simultaneous execution of steps 7 and 8. For example, a step L (described hereinafter) may be inserted between steps 8 and 9 when the method adopts knowledge acquisition solution 1.

The method according to the invention is thus able to comprise, depending on the value of the predictive capability error $E_C$ of said treatment algorithm using a learning method:

a step 1 for determining the risk prediction solution to be adopted, and involving testing the value of the most recently known predictive capability error $E_C$ (for example: recorded in memory or input by the physician) and, if the value of the error is greater than a predefined threshold SE, performing at least following steps 2 to 12 (preferably in this order, that is to say in numerical order), otherwise performing at least steps 2, 3, 5, 6 and 7, preferably in this order.

Preferably, when the value of the error $E_C$ is lower than said predefined threshold SE, at least steps 2, 3, 4, 5, 6 and 7 are performed, preferably in this order. This preferred variant is shown in FIG. 2 by double white-headed arrows between steps 3-4 and 4-5.

The value of the most recently known predictive capability error $E_C$ preferably corresponds to the last value recorded in a previous iteration of the method.

However, in some variants of the method, the physician may record a value of his choice for the predictive capability error $E_C$ before the method is launched, and this manually entered value will then be considered to be the most recently known error.

Preferably, in order for the phase of developing and training the treatment algorithm using a learning method to be able to take place, the initial value (value in the first iteration of the method, corresponding to the patient $P_1$) of the predictive capability error $E_C$ is defined as being greater than the predefined threshold SE.

Advantageously, said predefined threshold SE is less than or equal to 20%.

Preferably, said predefined threshold SE is less than or equal to 5%.

a step 2 of acquiring at least one representation R of a vascular region of interest V of said patient $P_i$. Advantageously, the representation R is chosen from among: 4D flow MRI sequence, angiography, cine-MRI and the vascular region of interest V is a vascular region at risk of an aneurysm, such as: region comprising the abdominal aorta and/or the thoracic aorta, region comprising a popliteal artery, region comprising the hepatic artery. The vascular region of interest V is preferably the region comprising the thoracic aorta.

a step 3 of reconstructing, from said representation R, at least one model M of said region of interest V from among: primary model MP, corrected model MC. The primary model MP corresponds precisely to said region of interest V (with its imperfections and/or its anomaly (or its anomalies) linked to the pathology affecting the patient), whereas the corrected model MC corresponds to a corrected version of said region of interest V, the correction involving removing the anomaly (the pathology) established in said representation R, such as: aneurysm, coarctation, etc., so as to obtain a model that corresponds to what the region of interest V should be if it were to be "healthy".

As will be discussed further on, using a corrected model makes it possible to identify predictive parameters of a vascular risk, for example parameters for which values that are particularly high are correlated with the development of an aneurysm.

a step 4 of generating, from said model M, at least one mesh T (TP, TC) of said region of interest V, that is to say generating at least:

a primary mesh TP corresponding to the primary model MP, and/or a mesh TC corresponding to the corrected model MC.

The constructed volumetric mesh (or meshes) is preferably of unstructured tetrahedral type for the regions of interest such as the macroscopic arteries, and of structured hexahedral type for the region of interest constituted by the aortic valve.

According to one particularly preferred variant of the invention, the meshes relating to the walls of the aorta and/or to the valve (that is to say the outside) are of hexahedral type, and the mesh relating to the flow area (that is to say the inside) is of tetrahedral type.

According to one variant of the invention, said step 4 of the method furthermore comprises a sub-step of evaluating and of validating the generated meshes, involving firstly studying the sensitivity of said mesh (or meshes) by varying (on their own or in combination) parameters such as: asymmetry, regularity, number of elements, and making it possible secondly to choose the most suitable set of mesh generation parameters.

Advantageously, the mesh (or meshes) generated when the method adopts solution 1 is voluminous, and the mesh (or meshes) generated when the method adopts solution 2 is areal.

a step 5 of extracting, from at least one model M (whether this is for example the primary model MP or the corrected model MC) and/or from at least one mesh T (whether this is for example a primary mesh TP or a corrected mesh TC or else another mesh), data DG in relation to the geometry of said vascular region of interest V. Advantageously, the data DG are extracted:

directly, from the model M and/or from the mesh T, indirectly, that is to say through calculation.

Advantageously, the data DG comprise at least one item of data from among:

the exploration length L, that is to say the length corresponding to the total horizontal projection of said model M, the height A of the center line arc, the diameter D of the aorta, the inner radius B of the aneurysm (perpendicular to the center line LC of the aneurysm), which corresponds to the radius of the center line of the aorta to the inner wall of the aneurysm (that is to say the wall exhibiting the smallest bulge), the outer radius C of the aneurysm (perpendicular to the center line LC of the aneurysm), which corresponds to the radius of the center line of the aorta to the outer wall of the aneurysm (that is to say the wall exhibiting the greatest bulge), the length of the aneurysm AL, that is to say the average length of the aneurysm, and/or the effective valvular area AVE over time (EOA: effective orifice area): this area is able to be calculated for example from the inflow, from a separate CFD study, from flow imaging or a catheter, the inflow, the outflow pressure.

a step 6 of forming a set of parameters JP to be analyzed, so as to evaluate the risks in said region of interest V, from at least one pre-recorded (fixed or variable) list of (predictive and/or non-predictive) parameters to be analyzed, Advantageously, at least some of the parameters JP are "local" parameters, that is to say the value of which depends, inter alia, on the position in the region of interest V. It is however not necessary for a value of the parameter to be defined for each node of the mesh of said region; for example, the values of some parameters may be defined for sections of a blood vessel (for example the aorta) in the region of interest.

Advantageously, when the method according to the invention adopts solution 1, the set of parameters JP is formed gradually, at least through selection from said fixed list.

Preferably, when the method according to the invention adopts solution 1, the set of parameters JP is able to contain predictive and non-predictive parameters.

Preferably, when the method according to the invention adopts solution 1, the set of predictive parameters SPP is formed through selection as defined above and/or through addition of at least one additional (predictive or non-predictive) parameter. The addition of at least one additional parameter results from inputting by the physician (the user, the researcher, the developer, etc.) and/or from an update by the method itself (following another step of the method: there may be for example looping of the method following step 7 and/or 8, which are described hereinafter). Advantageously, when the method according to the invention adopts solution 1, the additional parameter that is added is recorded in said list (for example so as to keep a log of the studied parameters).

Advantageously, when the method according to the invention adopts solution 2, the set of parameters JP is formed at least through selection from said list. Preferably, when the method according to the invention adopts solution 2, the set of parameters JP contains exclusively predictive parameters.

Preferably, when the method according to the invention adopts solution 2, the set of parameters JP is formed through selection as defined above and through addition of at least one additional predictive parameter.

Advantageously, when the method according to the invention adopts solution 2, the additional parameter is recorded in said list (for example so as to keep a log of the studied parameters).

The list is thus able to comprise, as it is formed, validated parameters (that is to say ones that are actually predictive) and/or non-validated parameters (that is to say ones that are assumed, correctly or incorrectly, to be predictive).

The parameter (or parameters) forming the set of parameters JP are preferably chosen, inter alia, from among:

wall shear stress (WSS), defined by the formula $\tau_w =$ $$\mu * \frac{du}{dy}_{y=0},$$

in which $\mu$ is the dynamic viscosity, u is the flow velocity parallel to the wall, and y is the distance to the wall, any parameter derived from the wall shear stress, oscillatory shear index (OSI), defined by the formula $$OSI = 0.5 * \left(1 - \frac{\left|\int_0^T \overrightarrow{WSS} dt\right|}{\int_0^T |\overrightarrow{WSS}| dt}\right),$$

time-averaged wall shear stress (AWSS), defined by the formula $$AWSS = \frac{1}{T} * \int_0^T |\overrightarrow{WSS}| dt,$$

time-averaged wall shear stress vector (AWSSV), defined by the formula $$AWSSV = \frac{1}{T} * \left|\int_0^T \overrightarrow{WSS} dt\right|,$$

wall shear stress at peak systole (WSSPS), spatial wall shear stress gradient SWSSG (spatial WSS gradient), which represents the spatial non-uniformity of the wall shear stress (WSS), and is defined by the formula $$SWSSG = \left(\frac{\delta WSSp}{\delta p}, \frac{\delta WSSq}{\delta q}\right),$$

in which the direction p corresponds to the direction of the WSS vector over the flow cycle, and the direction q is perpendicular to p, hemodynamic index GON (gradient oscillatory number: GON), which quantifies the magnitude of the oscillatory forces in tension and compression, and is defined by the formula $$GON = 1 - \frac{\left|\int_0^T SWSSG dt\right|}{\int_0^T |SWSSG| dt},$$

mid-systolic deceleration aneurysm formation index (AFI), which quantifies the cosine of the angle between the WSSi vectors (WSSi corresponds to the WSS at a given instant i of the flow cycle) and AWSSV, and is defined by the formula $$AFI = \frac{WSSi \times AWSSV}{|WSSi| \times |AWSSV|},$$

Inlet pressure (IP), obtained for example using Darcy's law (flow rate linearly proportional to the pressure difference between two points and inversely proportional to hydraulic resistance), using the resistance of the blood vessel of interest, said resistance being calculated for example using Poiseuille's law on the basis of the observation of the fact that an aortic aneurysm leads to a local increase in the diameter of the vessel, it is possible to describe a group of parameters linked to a section $S_C$ of the aorta:

wall shear stress in relation to said section $S_C$ ($S_C$WSS):

$$S_C WSS = \int_{S_C} WSS dS,$$

spatial wall shear stress gradient in relation to said section $S_c$ ($S_C$SWSSG):

$$S_C SWSSG = \int_{S_C} |SWSSG| dS,$$

time-averaged wall shear stress in relation to said section $S_C$ (AS$_C$WSS):

$$AS_C WSS = \int_T S_C WSS dt,$$

time-averaged spatial wall shear stress gradient in relation to said section $S_C$ (AS$_C$SWSSG):

$$AS_C SWSSG = \int_T SWSSG \, dt,$$

wall shear stress at peak systole, in relation to said section $S_C$ ($S_C$WSSPS)

spatial wall shear stress gradient at peak systole in relation to said section $S_c$ ($S_C$SWSSGPS), standard deviation of the wall shear stress in relation to said section $S_C$ (DS$_C$WSS):

$$\sigma(S_C WSS) = \sqrt{\int_{S_C} (WSS - S_C WSS)^2 dS},$$

standard deviation of the spatial wall shear stress gradient in relation to said section $S_c$ (DS$_C$SWSSG):

$$\sigma(S_C SWSSG) = \sqrt{\int_{S_C} (|SWSSG| - S_C SWSSG)^2 dS},$$

standard deviation of the time-averaged wall shear stress in relation to said section $S_C$ (ADS$_C$WSS) :

$$ADS_C WSS = \int_T \sigma(S_C WSS) dt,$$

standard deviation of the time-averaged spatial wall shear stress gradient in relation to said section $S_C$ (ADS$_C$SWSSG):

$$ADS_C SWSSG = \int_T \sigma(S_C SWSSG) dt$$

standard deviation of the wall shear stress at peak systole, in relation to said section $S_C$ (DS$_C$WSSPS), standard deviation of the spatial wall shear stress gradient at peak systole in relation to said section $S_C$ (DS$_C$SWSSGPS).

An aortic aneurysm results in a local increase in the diameter of the blood vessel. Thus, in one advantageous embodiment of the invention, the parameters of the set JP, or at least some of them, are based on the wall shear stress in a section of the aorta. This leads to the use of (at least) the following parameters:

the time-averaged wall shear stress in relation to a section of the vascular region of interest;

the time-averaged spatial wall shear stress gradient in relation to said section of the vascular region of interest;

the wall shear stress at peak systole in relation to said section of the vascular region of interest; and the spatial wall shear stress gradient at peak systole in relation to said section of the vascular region of interest.

It also appears beneficial to consider the disparity of the wall shear stress in a section of the aorta, notably with consideration to the fact that aortic aneurysms do not generally exhibit a uniform increase in diameter within a section. This leads to the use of (at least) the following parameters:

the standard deviation of the time-averaged wall shear stress in relation to a section of the vascular region of interest;

the standard deviation of the time-averaged spatial wall shear stress gradient in relation to said section of the vascular region of interest;

the standard deviation of the wall shear stress at peak systole in relation to said section of the vascular region of interest; and the standard deviation of the spatial wall shear stress gradient at peak systole in relation to said section of the vascular region of interest.

a step 7 of:

Determining the predictive risk numerical data $DN_A$ associated with at least one parameter of the set of parameters JP formed in step 6, that is to say calculating the numerical values of said parameters, by way of said treatment algorithm using a learning method, from at least the data DG in relation to the geometry of said vascular region of interest V, assigning a risk level $NR_A$ to said parameter (or to said parameters) of the set of parameters JP, from among a scale of risk levels, generating a risk model $MR_A$ in said region of interest V at least for each parameter of the set of parameters JP from said determined numerical data $DN_A$.

Advantageously, the treatment algorithm using a learning method functions like an emulator that approximates the numerical data (values) of the parameters of the set of parameters JP as a function of the data that are provided thereto.

Thus, once it has been constructed and validated, the emulator is intended to be used (post-construction phase, solution 2), inter alia, to: provide statistics regarding the output variables, and/or identify the relative importance of each input variable, and/or identify sets of input parameters leading to particular conditions at output.

Advantageously, the treatment algorithm using a learning method uses a technique such as: neural networks, notably multilayer perceptron neural networks, decision trees, Bayesian networks, self-adaptive maps.

For example, an algorithm based on Bayesian networks and a multivariate approach (which constitutes a data mining method) has proven to be effective in CFD flow studies, in this respect see:

V. B. Kolachalama, N. W. Bressloff, and P. B. Nair. *Mining data from hemodynamic simulations via Bayesian emulation*. BioMedical Engineering OnLine, vol. 6, article 47, 2007.

More recently, back propagation-trained multilayer perceptron neural networks hare delivered promising results in the prediction of flow parameters, such as wall shear stresses, from geometric parameters. In this respect see:

N. Jankovic, M. Radovic, D. Petrovic, N. Zdravkovic, and N. Filipovic. *Mining data from CFD simulations of aneurysm and carotid bifurcation models*. J. of the Serbian Soceity for Computational Mechanics. 2012; 6(2): 133-144.

This method has been applied to the case of an aneurysm using 9 input neurons and 5 output neurons, on a set of 3346 learning examples. After 1000 iterations, the error was 3.51%.

The self-organized map method also appears promising, in this respect see:

S. Morizawa, K. Shimoyama, S. Obayashi, K. Funamoto, and T. Hayase, *Implementation of visual data mining for unsteady blood flow field in aortic aneurysm*. J. Vis. 2011; 14: 393-398.

The predictive numerical data DNA are preferably determined at each point of the generated mesh (or meshes) (primary TP and/or corrected TC or other meshes), inter alia, in step 4, and/or at each time step. For example, a cardiac cycle (which usually lasts 0.8 seconds) is broken down into a number of time steps of between ten and one hundred, and preferably into twenty time steps.

a step 8 of determining the predictive risk numerical data DNE associated with at least one parameter of said set of parameters JP formed in step 6, that is to say calculating the numerical values of said parameters, through a fluidic study comprising at least one CFD study from at least:

a set of meshes comprising at least one mesh generated in step 4, and/or at least one set of input-output conditions SC, and/or data DG in relation to the geometry of said vascular region of interest V, and:

assigning a risk level $NR_E$ to said parameter (or to said parameters) of the set of parameters JP, from among a scale of risk levels, generating a risk model $MR_E$ in said region of interest V at least for each parameter of the set of parameters JP from said determined numerical data DNE.

Advantageously, according to the invention, the numerical data $DN_E$ are calculated locally (that is to say by calculating for example a value of the parameter (or parameters) at each mesh point or an average value over a defined area) and/or globally over time (that is to say by calculating for example a value of the parameter (or parameters) for each time step or an average value over the whole cardiac cycle). As the numerical data $DN_E$ are calculated locally, the numerical data $DN_A$ are dependent on the position. It is thus possible to create a map of the distribution of these values. This map may be displayed on a computer screen, for example by way of a color code or of a gray scale.

The risk levels $NR_E$ may be determined from a spatial correlation between the calculated values $DN_E$ of the parameters of the set JP and the pathological anomalies of the region of interest. For example, if a parameter calculated from the corrected model MC exhibits particularly high values at the locations where the primary model MP exhibits an anomaly (for example an aneurysm), it is possible to assume that the parameter in question is predictive of the formation of an aneurysm. Specifically, the corrected model constitutes an approximation of the conditions of the patient before the formation of the aneurysm (more generally of the pathology)—but when the factors at the origin thereof were already present. In this case, high (low) values of the parameter will be associated with a high (low) risk level. As the risk levels are defined locally, it is possible to create a map therefrom and to display it on a computer screen, for example by way of a color code or of a gray scale.

Advantageously, according to some variants of the invention, the fluidic study comprises a computational fluid dynamics (CFD) study.

The fluidic study preferably comprises both a computational fluid dynamics study and a fluid structure-interaction (FSI) study.

Advantageously, the fluidic study involves at least solving the Navier-Stokes equations when the model is macroscopic, and solving the BGK-Boltzmann equation when the model is mesoscopic. Preferably, when the vascular region of interest V is the aorta, the movements of the walls are taken into account by solving a hyperelastic neo-Hookean model.

Thus, according to the variants of the invention, numerical data $DN_E$ are determined that may be: data $DN_{EC}$ corresponding to the CFD fluidic study, and/or data $DN_{EF}$ corresponding to the FSI fluidic study.

Advantageously, the set of input-output conditions SC comprises, inter alia, at least one parameter from among: Reynolds number at peak systolic at inlet, effective valvular area (EOA) at inlet, outlet resistance.

The set (or sets) of input-output conditions SC is (are) preferably:
- pre-recorded in memory, and/or
- input manually by the physician, and/or
- the result of an evaluation and/or validation step L (described hereinafter).

Advantageously, according to the variants of the invention, the set (or sets) of input-output conditions SC is: selected from a pre-existing list and/or input manually upon request and/or obtained by performing a stochastic modification of at least one parameter of a set of initial input-output conditions SCI.

Advantageously, the set of input-output conditions SC comprises, inter alia, at least one parameter from among: Reynolds number at peak systolic at inlet, effective valvular area (EOA) at inlet, outflow resistance, inflow, profile of the velocity at inlet.

The predictive numerical data $DN_E$ are preferably determined at each point of the generated mesh (or meshes) (primary TP and/or corrected TC) in step 4 and/or at each time step.

In sophisticated variants of the invention, the group of meshes furthermore comprises at least one adapted mesh TA formed from said primary mesh TP by performing a stochastic modification of at least one parameter linked to said primary mesh TP.

Advantageously, the fluidic study takes into account, inter alia, at least one element from among: the movement of the aorta due to respiration and to cardiac movements, the elasticity of the aorta.

a step 9 of evaluating the predictive capability error $E_C$ of the treatment algorithm using a learning method in relation to the fluidic study (which serves as a reference, since it describes the real behavior and produces valid results), by comparing at least the results of steps 7 and 8, and recording the value of the predictive capability error $E_C$.

Advantageously, the evaluation of the predictive capability error $E_C$ of the treatment algorithm using a learning method is carried out at least by evaluating the error between:
- the predictive risk numerical data (numerical values) $DN_E$ calculated through a fluidic study and that constitute the reference values (since these are real values)
- the predictive risk numerical data $DN_A$ (numerical values) calculated by said treatment algorithm using a learning method and that constitute the values to be optimized.

Recording the value of the error $E_C$ may involve either deleting the previously recorded value or recording the value in a list by assigning it an indicator signifying that it is the most recently calculated value.

a step 10 of training said treatment algorithm using a learning method by providing it at least with the results of step 8.

a step 11 (not shown in FIG. 2) of recording all of the data that are obtained in a patient case database in a data storage unit.

In more detail, step 9 involves comparing:
- the numerical data (numerical values) DN ($DN_A$ and/or $DN_E$) of the parameter (or parameters) of the set of parameters JP to be analyzed and/or estimating the error between said numerical data DN, so as to verify whether their correspondence is sufficient, and/or
- the risk models MR, so as to verify whether the correspondence between the risk areas is sufficient.

In this context (step 9), the comparison of the numerical data DN may involve:
- comparing the numerical data DN, so as to verify whether the correspondence between:
  - the reference numerical data $DN_E$ resulting from the fluidic study, and
  - the (predicted) numerical data $DN_A$ resulting from the treatment algorithm using a learning method to be optimized
  is satisfactory, and/or
- estimating the error (for example in terms of percentage, in terms of level, etc.) between said numerical data $DN_E$ resulting from the fluidic study and $DN_A$ resulting from the treatment algorithm using a learning method to be optimized, and/or
- comparing the numerical data DN, so as to verify whether the correspondence between:
  - the numerical data DN associated with the model (or models) resulting from the real case (or cases) (that is to say resulting from the primary mesh TP), and
  - the digital data DN associated with the model (or models) resulting from the simulated case (or cases) (that is to say resulting from the corrected mesh TC and/or from other meshes, for example: adapted meshes TA)
  is satisfactory, and/or
- estimating the error (for example: in terms of percentage, or else in terms of deviation between the coordinates of the centers of the real and simulated risk areas, etc.) between said real numerical data DN and said simulated numerical data.

Also in this context (step 9), comparing the risk models MR may involve:
- comparing the risk models $MR_A$ and $MR_E$, so as to verify whether the correspondence between:
  - the reference risk areas, present on the model (or models) $MR_E$ resulting from the fluidic study, and
  - the risk areas present on the model (or models) $MR_A$ resulting from the treatment algorithm using a learning method to be optimized
  is satisfactory, and/or
- estimating the error (for example: in terms of percentage reflecting the deviation between the surface areas calculated for the risk areas, or else in terms of deviation between the centers of the risk areas) between said risk areas resulting from the fluidic study and said risk areas resulting from the treatment algorithm using a learning method to be optimized, and/or comparing the risk models so as to verify whether the correspondence between:
the reference risk areas present on the model (or models) resulting from the real case (or cases) (that is to say resulting from the primary mesh TP), and the risk areas present on the model (or models) resulting from the simulated case (or cases) (that is to say resulting from the corrected mesh TC and/or from other meshes, for example: adapted meshes TA)

is satisfactory, and/or estimating the error (for example: in terms of percentage reflecting the deviation between the surface areas calculated for the risk areas, or else in terms of deviation between the centers of the risk areas) between said real risk areas said simulated risk areas.

When the evaluation method concerns the direct application (solution 2) of said treatment algorithm using a learning method to the data of a patient, it is possible to directly obtain (that is to say without excessively long calculations in comparison with fluidic studies) at least one risk model $MR_A$ as a decision assistance support for physicians.

Advantageously, in advanced variants of the risk evaluation method according to the invention, the determination, by said treatment algorithm using a learning method, of the numerical data DN ($DN_E$, $DN_A$) is furthermore performed from a set of parameters JSP specific to said patient $P_i$. Advantageously, said set of parameters JSP specific to said patient $P_i$ is acquired before the method. Said set of specific parameters JSP comprises for example:

the age of the patient,
the gender of the patient,
size of the patient,
weight of the patient,
existence and nature of connected pathologies (stenosis, thrombosis, aortic tear, hyperviscosity, etc.).

Advantageously, in advanced variants of the risk evaluation method according to the invention, if the value of the predictive capability error is lower than the predefined threshold (solution 2), the method furthermore involves performing steps 8, 10 and 11 in this order, after step 7.

Advantageously, in advanced variants of the risk evaluation method according to the invention, said method furthermore comprises at least one step L of evaluating and/or validating the parameter (or parameters) of the set of parameters JP to be analyzed (solution 1 and/or solution 2).

Preferably, the step (or steps) L of evaluating and/or validating the parameter (or parameters) of the set of parameters JP to be analyzed are performed exclusively when the method adopts knowledge acquisition solution 1 (value of the predictive capability error $E_C$ greater than the predefined threshold SE).

Advantageously, the step (or steps) L of evaluating and/or validating the parameter (or parameters) of the set of parameters JP is performed after step 8 and is based on the utilization of the results resulting from at least one step from among: step 8, additional study (or studies).

A (or the) additional study (or studies) may be for example (and without limitation):

carrying out a study (CFD and/or FSI and/or other study, etc.) on a phantom (that is to say a physical replica, for example made of silicone, intended for experimental purposes) corresponding to the studied patient case, carrying out a study (CFD and/or FSI and/or other study, etc.) based on at least one other representation R' of the studied patient case (for example: post-operation images).

Thus, when the second additional study example is chosen, the results of the fluidic studies on the patient case before operating (step 8) and after operating (additional study) are compared.

Advantageously, the step L of evaluating and/or validating the parameter (or parameters) of the set of parameters JP is based on utilizing the results resulting from step 8 and from at least one additional study, and involves comparing:

the numerical data (numerical values) $DN_E$ resulting from the fluidic study (step 8) and the numerical data resulting from said additional study, so as to verify whether their correspondence is sufficient, and/or the risk model $MR_E$ resulting from the fluidic study (step 8) and the risk model (or models) resulting from said additional study, so as to verify whether the correspondence between the risk areas is sufficient.

Whether experimental (on a phantom) or numerical, the additional study furthermore makes it possible to more quantitatively determine the relationship linking the numerical values of the parameters and the risk levels.

Preferably, when step L is used as a step of evaluating the parameter (or parameters) of the set of parameters JP, it gives the physician information regarding the validity of the set of parameters JP formed in step 6, and it involves at least:

comparing (as described in the previous paragraph) the numerical data DN and/or the risk models obtained from the parameter (or parameters) of the set of parameters JP to be analyzed, and on the basis of the comparison, assigning a predictive accuracy level $N_P$ to said parameter (or to said parameters) of the set of parameters JP to be analyzed, from among a scale of accuracy levels.

On this informative basis (predictive accuracy level $N_P$ the parameters), the physician is able to readjust the set of parameters JP.

Preferably, when step L is used as a step of validating the parameter (or parameters) of the set of parameters JP, it involves at least:

varying the set of input-output conditions SC used in step 8 (for example by performing a stochastic modification of at least one parameter of said set SC), comparing (as described in the previous paragraph) the numerical data DN and/or the risk models obtained from the parameter (or parameters) of the set of parameters JP to be analyzed, and on the basis of the comparison, assigning a predictive accuracy level $N_P$ to said parameter (or to said parameters) of the set of parameters JP to be analyzed, from among a scale of accuracy levels. updating at least the set of parameters JP to be analyzed, formed in step 6, such that it includes the parameter (or parameters) having a sufficient predictive accuracy level $N_P$.

The assignment of a predictive accuracy level $N_P$ is preferably performed in a binary manner: either the parameter is considered to be predictive or it is not.

Advantageously, in sophisticated variants of the method, the update involves updating a list associating:

the parameters of the set of parameters JP having the highest accuracy level $N_P$, and/or the corresponding input-output conditions SC allowing said highest accuracy level $N_P$ to be achieved.

Preferably, the updating of the set of parameters JP to be analyzed, formed in step 6, is performed such that it includes exclusively the parameter (or parameters) having the highest predictive accuracy level $N_P$.

Advantageously, when step L is used as a step of validating the parameter (or parameters) of the set of parameters JP, it may either:
- be performed after step 8 and before step 11, without influencing steps 9 and 10,
- be performed after step 8 and define the move to step 9.

Preferably, when step L is used as a step of validating the parameter (or parameters) of the set of parameters JP, it imposes looping of the method on successive steps 8 and L for as long as the set of input-output conditions SC (applied to the fluidic study) does not allow the parameters of the set of parameters JP to reach a sufficient accuracy level $N_P$. This looping is shown in FIG. 2 by way of a double-line arrow that symbolizes the updating of the set of parameters JP (last sub-step of validation step L), and does not exist when step L is used as a step of evaluating the parameter (or parameters) of the set of parameters JP.

Advantageously, the accuracy level $N_P$ is chosen depending on the studied pathology (or on the cluster of pathologies).

Advantageously, an accuracy level $N_P$ is chosen for a group of parameters (a combination of some of the parameters of the set of parameters JP, or the entire set of parameters) of the set of parameters JP.

An accuracy level $N_P$ is preferably chosen for each parameter of the set of parameters JP.

Preferably, for each parameter of the set of parameters JP, the accuracy level $N_P$ is chosen depending on the studied pathology (or on the cluster of pathologies).

The accuracy level $N_P$ is preferably considered to be sufficient when there is a difference of 20% or less between the numerical data DN and/or the simulated and expected (real) risk models, corresponding to the parameter under consideration (belonging to the set of parameters JP).

Advantageously, when at least one set of input-output conditions SC is identified as allowing the parameters of the set of parameters JP to reach a sufficient accuracy level $N_P$ (step L is used as a validation step), and/or when the correspondence between the numerical data DN and/or the risk models is sufficient, the method moves to step 9.

In light of all of the features outlined above, a person skilled in the art will appreciate the advantages afforded by the invention, and the advantage of using it to the benefit of patients affected by bicuspid conditions.

Of course, the steps described above are not limiting, and a person skilled in the art will know how to choose, combine and/or supplement the steps most appropriate for risk evaluation in a vascular region of interest, depending on the targeted application.

Moreover, the invention relates to a system for risk evaluation in a vascular region of interest V, able to implement a risk evaluation method as described above, and comprising:
- at least one medical imaging means, intended to image the vascular region of interest of the patient (or patients),
- at least one data storage unit, intended to store data,
- a data processing unit able to communicate with said medical imaging means and/or with said data storage unit, and able to process the data in accordance with the method provided by the invention, so as inter alia to produce (generate) risk models MR indicating and/or making it possible to evaluate, predictively, the risk level NR (aneurysm rupture, coarctation, etc.) and the associated risk areas (the evaluation taking place spatially and/or temporally), and intended to serve as an assistance support for the medical decision-making of a physician.

Advantageously, said data storage unit is intended to store data:
- that are external, and/or
- that result from the method as such, for example inter alia: the representations R, the models M, the value (or values) of the predictive capability error of the treatment algorithm using a learning method, the sets of predictive parameters, the sets of parameters specific to the patients.

Ultimately, a person skilled in the art will appreciate the usefulness and the ease of use of a risk evaluation method according to the invention, in an adapted risk evaluation system, in comparison with existing methods and systems.

It is readily understood that the method according to the invention is particularly effective for obtaining precise models, which are even dynamic (spatially and temporally), of risks incurred by the patient, such as the risk of aneurysm rupture. This method may moreover be used to treat DICOM images originating directly (or indirectly, for example via digital conversion) from imaging systems such as: MRI apparatus, angiography apparatus, etc.

Of course, it is obvious that the present invention is not limited to just the described forms of execution; on the contrary, it incorporates all variant embodiments and application variants thereof that comply with the same principle.

The invention claimed is:

1. A method for risk evaluation in a vascular region of interest V, implementing a treatment algorithm using a learning method, wherein it comprises the following steps for each successive patient case $P_i$ from among a group of patients $\{P_1, \ldots, P_i, \ldots, P_n\}$:

Step 1. testing the value of the predictive capability error $E_C$ of said treatment algorithm using a most recently known learning method, which value is defined so as to be greater than a predefined threshold SE in the first iteration of the method, and if the value of the error $E_C$ is greater than said predefined threshold SE, performing at least following steps 2 to 11, otherwise performing at least following steps 2-3-5-6-7, Step 2. acquiring at least one representation R of a vascular region of interest V of said patient $P_i$, Step 3. reconstructing, from said representation R, at least one model M of said region of interest V, said model corresponding to the geometry of said region of interest corrected for any possible pathological anomaly;

Step 4. generating, from said model M, at least one mesh T (TP, TC) of said region of interest V, Step 5. extracting, from at least one model M and/or from at least one mesh T, data DG in relation to the geometry of said vascular region of interest V, Step 6. forming a set of parameters JP to be analyzed, so as to evaluate the risks in said region of interest V, from at least one pre-recorded list of parameters, Step 7. determining the predictive risk numerical data $DN_A$ associated with at least one parameter of said set of parameters JP formed in step 6, by way of said treatment algorithm using a learning method, from at least the data DG in relation to the geometry of said vascular region of interest V, assigning a risk level $NR_A$ to said parameter from among a scale of risk levels, and generating a risk model $MR_A$ in said region of interest V at least for each parameter of said set of parameters JP from said determined numerical data $DN_A$, Step 8. determining the predictive risk numerical data $DN_E$ ($DN_{EC}$, $DN_{EF}$), associated with at least one parameter of said set of parameters JP formed in step 6, through a fluidic study comprising at least one CFD study, from at least one group of meshes comprising at least one mesh generated in step 4 and from at least one set of adapted input-output conditions SC, assigning a risk level $NR_E$ to said parameter from among a scale of risk levels, and generating a risk model $MR_E$ ($MR_{EC}$, $MR_{EF}$) in said region of interest V at least for each parameter of said set of parameters JP from said determined numerical data $DN_E$ ($DN_{EC}$, $DN_{EF}$), Step 9. evaluating the predictive capability error $E_C$ of the treatment algorithm using a learning method in relation to the fluidic study, by comparing at least the results of steps 7 and 8, and recording the value of the capability error $E_C$, Step 10. training said treatment algorithm using a learning method by providing it at least with the results of step 8, Step 11. recording all of the data that are obtained in a patient case database in a data storage unit.

2. The risk evaluation method as claimed in claim 1, wherein the determination, by said treatment algorithm using a learning method, of the numerical data DN ($DN_E$, $DN_A$) is furthermore performed from a set of parameters JSP specific to said patient $P_i$.

3. The risk evaluation method as claimed in claim 1, wherein the group of meshes used in step 8 furthermore comprises at least one adapted mesh TA formed from said primary mesh TP by performing a stochastic modification of at least one parameter linked to said primary mesh TP.

4. The risk evaluation method as claimed in claim 1, wherein, if the value of the predictive capability error $E_C$ is lower than the predefined threshold SE, steps 8, 10 and 11 are also performed, in this order, after step 7.

5. The risk evaluation method as claimed in claim 1, wherein the meshes relating to the outer walls of the vascular region of interest are of hexahedral type, and the mesh relating to the inner flow area is of tetrahedral type.

6. The risk evaluation method as claimed in claim 1, furthermore comprising at least one step L of evaluating and/or validating the parameter or parameters of the set of parameters JP to be analyzed, performed if the value of the predictive capability error $E_C$ is greater than the predefined threshold SE and after step 8.

7. The risk evaluation method as claimed in claim 6, wherein step L is a step of validating parameters of the set of parameters JP to be analyzed, and comprises the following operations:

varying the set of input-output conditions SC used in step 8, comparing the numerical data DN and/or the risk models obtained from the parameter or parameters of the set of parameters JP to be analyzed, on the basis of the comparison, assigning a predictive accuracy level $N_P$ to said parameter or to said parameters of the set of parameters JP to be analyzed, from among a scale of accuracy levels, and updating at least the set of parameters JP to be analyzed, formed in step 6, such that it includes the parameter or parameters having a sufficient predictive accuracy level $N_P$.

8. The risk evaluation method as claimed in claim 7, wherein there is looping on successive steps 8 and L for as long as the set of input-output conditions SC does not allow the parameters of the set of parameters JP to reach a sufficient accuracy level $N_P$, and wherein, when at least one set of input-output conditions SC is identified as allowing the parameters of the set of parameters JP to reach a sufficient accuracy level $N_P$, and/or when the correspondence between the numerical data DN and/or the risk models is sufficient, the method moves to step 9.

9. The risk evaluation method as claimed in claim 6, wherein said step L of evaluating and/or validating the parameter or parameters of the set of parameters JP to be analyzed comprises carrying out an additional study on a phantom and comparing the results of the fluidic study of step 8 with the results of the additional study.

10. The risk evaluation method as claimed in claim 1, wherein the learning method is a data mining method and wherein, if the value of the error $E_C$ is greater than said predefined threshold SE, steps 2 to 11 are performed in this order, otherwise at least steps 2-3-5-6-7 are performed in this order.

11. The risk evaluation method as claimed in claim 1, wherein said set of parameters JP comprises at least the following parameters:

the time-averaged wall shear stress in relation to a section of the vascular region of interest;

the time-averaged spatial wall shear stress gradient in relation to said section of the vascular region of interest;

the wall shear stress at peak systole in relation to said section of the vascular region of interest; and the spatial wall shear stress gradient at peak systole in relation to said section of the vascular region of interest.

12. The risk evaluation method as claimed in claim 1, wherein said set of parameters JP comprises at least the following parameters:

the standard deviation of the time-averaged wall shear stress in relation to a section of the vascular region of interest;

the standard deviation of the time-averaged spatial wall shear stress gradient in relation to said section of the vascular region of interest;

the standard deviation of the wall shear stress at peak systole in relation to said section of the vascular region of interest; and the standard deviation of the spatial wall shear stress gradient at peak systole in relation to said section of the vascular region of interest.

13. The risk evaluation method as claimed in claim 1, wherein the treatment algorithm using a learning method that is used in step 7 is chosen from among: a Bayesian network algorithm, a multilayer perceptron neural network and a self-adaptive map.

14. The risk evaluation method as claimed in claim 1, wherein the fluidic study of step 8 comprises at least one fluid-structure interaction study.

15. The risk evaluation method as claimed in claim 1, wherein the vascular region of interest includes at least one region of the aorta of the patient.

16. The risk evaluation method as claimed in claim 1, wherein the evaluated risk is a risk of aneurysm rupture.

17. The risk evaluation method as claimed in claim 1, wherein at least one parameter of said set of parameters JP is a local parameter, and wherein, in step 8, at least one risk level $NR_E$ is associated with said parameter based on a spatial correlation between a spatial distribution of the calculated values $DN_E$ of said parameter and at least one pathological anomaly of the region of interest.

18. A system for risk evaluation in a vascular region of interest V, implementing a risk evaluation method as claimed in claim 1, comprising:
- at least one medical imaging means, intended to image the vascular region of interest V of the patient (or patients),
- at least one data storage unit,
- a data processing unit able to communicate with said medical imaging means and/or with said data storage unit, and able to process the data in accordance with the method provided by the invention, so as inter alia to produce risk models MR indicating the risk level NR and the associated areas, and intended to serve as an assistance support for the medical decision-making of a physician.

\* \* \* \* \*